United States Patent
Aizawa et al.

(12) 
(10) Patent No.: US 6,555,670 B1
(45) Date of Patent: Apr. 29, 2003

(54) TESTIS-SPECIFIC GENE

(75) Inventors: Akira Aizawa, Maebashi (JP); Akiko Kawakami, Maebashi (JP); Toshihiko Kondo, Maebashi (JP)

(73) Assignees: Livestock Improvement Association of Japan, Inc., Gunma-ken (JP); President of Gunma University, Gunma-ken (JP)

( * ) Notice: Subject to any disclaimer, the term of this patent is extended or adjusted under 35 U.S.C. 154(b) by 0 days.

(21) Appl. No.: 09/965,599

(22) Filed: Sep. 26, 2001

(30) Foreign Application Priority Data

Oct. 3, 2000 (JP) ........................................ 2000-303994

(51) Int. Cl.$^7$ ..................... C07H 21/04; A61K 31/7088
(52) U.S. Cl. .................... 536/23.5; 536/23.1; 536/23.2; 514/44
(58) Field of Search ........................... 514/44; 536/23.1, 536/23.2, 23.5

(56) References Cited

FOREIGN PATENT DOCUMENTS

| WO | 99/09168 | 2/1999 | ........... C12N/15/12 |
|---|---|---|---|
| WO | 99/27091 | 6/1999 | ........... C12N/15/12 |

OTHER PUBLICATIONS

Davisson M.T. X–linked genetic homologies between mouse and man. Genomics. 1987 Nov.;1(3):213–227.*

Graves and Watson Mammalian sex chromosomes: evolution of organization and function. Chromosoma. 1991 Nov.;101(2):63–8.*

Accession, AV041341, EST Nov. 23, 1999.*

Accession, AV260338, EST, Nov. 04, 1999.*

Judith L. Leatherman et al., "Indentification of a mouse germ cell–less homologue with conserved activity in Drosphila" Mechanisms of Development, col. 92, No. 2, Apr. 2000, pp. 145–153.

Database EMBL 'Online! Oct. 1, 1993, Database accession No. QO1820XP002192737, Germ Cell–Less Protein. CGL or CG8411. Drosphila melanogaster (Fruit fly), Abstract.

Database EMBL 'Online! Nov. 2, 2000, Database Accession No. AF198534 SP002192738, Homo sapiens germ cell–less protein (GLC) mRNA, partial cds. Nili E et al., "The human germ cell–less (HGCL): a candidate gene for Alstrom syndrom" unpublished Abstract.

Database EMBL 3 Online! Jun. 1, 2001, Database Accession No. Q99N66 SP002192739 Mouse Germ Cell–Less Haploid Specific. MDCLH Aizawa et al., "Molecular cloning of a novel mouse germ cell–less homologue expressing haploid specifically in mouse testis".

Tohru Kimura et al., Molecular Cloning and Genomic Organization of Mouse Homologue of Drosphila germ cell-less and Its Expression of Germ Lineage Cells.

* cited by examiner

*Primary Examiner*—James Ketter
*Assistant Examiner*—Daniel M Sullivan
(74) *Attorney, Agent, or Firm*—Darby & Darby

(57) ABSTRACT

The invention provides a gene specifically expressed in haploid cells of the testis. The gene is located on the X-chromosome of a mammal, is specifically expressed in haploid cells of the testis, has a base sequence which can hybridize, under stringent conditions, with DNA including a base sequence in SEQ ID NO: 1, and encodes a protein including an amino acid sequence having a homology of at least 25% with an amino acid sequence encoded by the drosophila gcl gene.

5 Claims, 13 Drawing Sheets

```
        10         20         30         40         50         60
ACAGCAATGCCTCAACCAAGAAGCCTCTGCGAGAGCTTGTTCTAGGAATTTTCATCAATG 70         80         90        100        110        120
GGGCTTTTAGTCAGCAGGGTCTTGAGATGCAGGGATTCCAGTCTGTTAGAGCCACAGCCA 130        140        150        160        170        180
GAAGCCATAGCCGGAGCCAGCTACATTCCTGGCAGTCGCAAGCGAAAAAGAAACAGTTTG 190        200        210        220        230        240
GAGGAGTTGGCAACAAGTTCTAATGTTCATGGACCTCAAAACCAGGGAATGTATCCACAT 250        260        270        280        290        300
CAAGTTCTCAACTACATCTACTGGAAAAGGGTTAAGATCTCATCTAATGATGCTTATCAA 310        320        330        340        350        360
AACTTATTTTGGACGGGCATGATAGCGACATTAAAATCCGTGCTCTGGGAAGAACATGG 370        380        390        400        410        420
TGTTTACACAAAGTATTTTTATGTCAGTCAGGCTACTTTGCTAACATTCTCAAAGGTACT 430        440        450        460        470        480
TGGAGAGAATCACACCATGGTGTTATAAATCTGATCATTAAGAATGAGGATATTGATACC 490        500        510        520        530        540
CGATCTCTGCATTTTGTGTTTGGTGCTCTGTACACGGATGCGGATTTGTCAATAACACCT 550        560        570        580        590        600
CTGGAAGTTCCTCAAGTTTTGGCAGCAGCATGCCTGCTTCGAGTGGATCGAGTAATTCAG 610        620        630        640        650        660
CAGTGTGAAGGAATCATGAAAGAAACTATCAACAGGAACACTGTGTGCTCCTATTATTTG 670        680        690        700        710        720
GCAGCAGAAACCTATAGATTAAAAGCTGTAAAGACGAGATGCTTTGAATGGCTTCTTTGC 730        740        750        760        770        780
AATTTGATGGTACATCCAAGTGTGGCACTTTACAAGGAAGTAGATATGAAGTTGATGTAT
```

```
         790        800        810        820        830        840
CTTCTAGCACTGTCTTCTGACTTACTAGTCATGCAAAAGGAGATTGATGTATATACCACA 850        860        870        880        890        900
CTAAAAATATGGATGATCCTTTATCTTAATCCATGCTGGAACGGAACCATGAAACAGCTT 910        920        930        940        950        960
TTACAACACGCAAACAACTGGCTTTCCACCCACATGGCATATATTGATAACATCAGTTTT 970        980        990       1000       1010       1020
CTTGAAAGTGAAGAAGGACTAATATTTCAACCAGTGTTTAAAAAGCTGAGATTTCAGCAC 1030       1040       1050       1060       1070       1080
ATCATCTGTGACTTGACTTCCACAACTATTCTTGAACAAGATCGACTAATACCTATGGCA 1090       1100       1110       1120       1130       1140
TGGTTGTCACCCATTTACAAACAACAGTGGTTGACTTTGCTGCGAACACAAGAATATGGG 1150       1160       1170       1180       1190       1200
GTAATTGGACCACAAGTTATCAATGAACAAGAACTTGAAGAATGCACCATGAGGTGTGGT 1210       1220       1230       1240       1250       1260
ACAATGATCCCCAAAGATGGAAGATATACTTGGAAGTGGTCAGTTGGACGACTTGGCTTT 1270       1280       1290       1300       1310       1320
CCTTTACGTGTGACCTTTACCAGGCAGTGTGTAATTTTAAGGCAACGGTGTCAGAGGTGT 1330       1340       1350       1360       1370       1380
GATGGTTCTGCTTGCCACAACCATATCCGAAATGTCATATTCAGAATAACTTTGGTGTGT 1390       1400       1410       1420       1430       1440
TTTGATTCCAACAAAAGAGTAACTTTCAGAAAGACAACAGGTTATAAAATCCTCACCTTT 1450       1460       1470       1480       1490       1500
GAATATAACGAGGAGCAAATTGTAATGAAATTGGATAGTGATGTTCTAACCTTCCCTATG
```

```
         1510       1520       1530       1540       1550       1560
TGTATATTCTGCAATTTCCTTTTTGTAAACCTAGGAAATGCAGAAAACAAGTAATCTTAT 1570       1580       1590       1600       1610       1620
CAATTATTAGACTGTAAGCATTTTACAAGTATTGAATGGCTCATTTAATATGAAGGCTGT 1630       1640       1650       1660       1670       1680
GTAATGACTACAGTGAGGAAGACCAAAAACAAATTCAATATTCTTTGGAGTCTAGTACCA 1690       1700       1710       1720       1730       1740
CCAGAAGTGACTGCTTCCCTCCATCACCTTATTTCCATGTATTTCTGAAGAAAACCTTTA 1750       1760       1770       1780       1790       1800
CTTCCAACAAAGTATTTGTCAAATCAAATAAACCTAATCTTCTGATTTAAATTTACCATC 1810       1820       1830       1840       1850       1860
GAGATCCAAGCTTGGAATGGAAATAAGAGACTATATTTGCAAGGTAAAACATCTCAAACA 1870       1880       1890       1900       1910       1920
ACTTGTTAAGTAGATTTGGCCCTAGCTAAAATTGAGACAAAATAAAATCATGCCATTGTT 1930       1940
GAAAAAAAAAAAAAAAAAAA
```

FIG. 2C

```
          10         20         30         40         50         60
MGLLVSRVLRCRDSSLLEPQPEAIAGASYIPGSRKRKRNSLEELATSSNVHGPQNQGMYP 70         80         90        100        110        120
HQVLNYIYWKRVKISSNDAYQNLFLDGHDSDIKIRALGRTWCLHKVFLCQSGYFANILKG 130        140        150        160        170        180
TWRESHHGVINLIIKNEDIDTRSLHFVFGALYTDADLSITPLEVPQVLAAACLLRVDRVI 190        200        210        220        230        240
QQCEGIMKETINRNTVCSYYLAAETYRLKAVKTRCFEWLLCNLMVHPSVALYKEVDMKLM 250        260        270        280        290        300
YLLALSSDLLVMQKEIDVYTTLKIWMILYLNPCWNGTMKQLLQHANNWLSTHMAYIDNIS 310        320        330        340        350        360
FLESEEGLIFQPVFKKLRFQHIICDLTSTTILEQDRLIPMAWLSPIYKQQWLTLLRTQEY 370        380        390        400        410        420
GVIGPQVINEQELEECTMRCGTMIPKDGRYTWKWSVGRLGFPLRVTFTRQCVILRQRCQR 430        440        450        460        470        480
CDGSACHNHIRNVIFRITLVCFDSNKRVTFRKTTGYKILTFEYNEEQIVMKLDSDVLTFP
             490
MCIFCNFLFVNLGNAENK
```

FIG. 3

SEQUENCE LISTING

<160> NUMBER OF SEQ ID NOS: 7

<210> SEQ ID NO 1
<211> LENGTH: 1940
<212> TYPE: DNA
<213> ORGANISM: Mus musculus

<400> SEQUENCE: 1

```
acagcaatgc ctcaaccaag aagcctctgc gagagcttgt tctaggaatt ttcatcaatg      60
gggcttttag tcagcagggt cttgagatgc agggattcca gtctgttaga gccacagcca     120
gaagccatag ccggagccag ctacattcct ggcagtcgca agcgaaaaag aaacagtttg     180
gaggagttgg caacaagttc taatgttcat ggacctcaaa accagggaat gtatccacat     240
caagttctca actacatcta ctggaaaagg gttaagatct catctaatga tgcttatcaa     300
aacttatttt tggacgggca tgatagcgac attaaaatcc gtgctctggg aagaacatgg     360
tgtttacaca aagtattttt atgtcagtca ggctactttg ctaacattct caaaggtact     420
tggagagaat cacaccatgg tgtttataaat ctgatcatta agaatgagga tattgatacc     480
cgatctctgc attttgtgtt tggtgctctg tacacggatg cggatttgtc aataacacct     540
ctggaagttc ctcaagtttt ggcagcagca tgcctgcttc gagtggatcg agtaattcag     600
cagtgtgaag gaatcatgaa agaaactatc aacaggaaca ctgtgtgctc ctattatttg     660
gcagcagaaa cctatagatt aaaagctgta aagacgagat gctttgaatg gcttctttgc     720
aatttgatgg tacatccaag tgtggcactt tacaaggaag tagatatgaa gttgatgtat     780
cttctagcac tgtcttctga cttactagtc atgcaaaagg agattgatgt ataccaca     840 ctaaaaatat ggatgatcct ttatcttaat ccatgctgga acggaaccat gaaacagctt     900
ttacaacacg caaacaactg gctttccacc cacatggcat atattgataa catcagtttt     960
cttgaaagtg aagaaggact aatatttcaa ccagtgttta aaaagctgag atttcagcac    1020
atcatctgtg acttgacttc cacaactatt cttgaacaag atcgactaat acctatggca    1080
tggttgtcac ccatttacaa acaacagtgg ttgactttgc tgcgaacaca agaatatggg    1140
gtaattggac cacaagttat caatgaacaa gaacttgaag aatgcaccat gaggtgtggt    1200
acaatgatcc ccaaagatgg aagatatact tggaagtggt cagttggacg acttggcttt    1260
```

-continued

```
cctttacgtg tgacctttac caggcagtgt gtaattttaa ggcaacggtg tcagaggtgt      1320
gatggttctg cttgccacaa ccatatccga aatgtcatat tcagaataac tttggtgtgt      1380
tttgattcca acaaagagt aactttcaga aagacaacag gttataaaat cctcacctt        1440 gaatataacg aggagcaaat tgtaatgaaa ttggatagtg atgttctaac cttccctatg      1500
tgtatattct gcaatttcct ttttgtaaac ctaggaaatg cagaaaacaa gtaatcttat      1560
caattattag actgtaagca ttttacaagt attgaatggc tcatttaata tgaaggctgt      1620
gtaatgacta cagtgaggaa gaccaaaaac aaattcaata ttctttggag tctagtacca      1680
ccagaagtga ctgcttccct ccatcacctt atttccatgt atttctgaag aaaccttta      1740 cttccaacaa agtatttgtc aaatcaaata aacctaatct tctgatttaa atttaccatc      1800
gagatccaag cttggaatgg aaataagaga ctatatttgc aaggtaaaac atctcaaaca      1860
acttgttaag tagatttggc cctagctaaa attgagacaa aataaaatca tgccattgtt      1920
gaaaaaaaaa aaaaaaaaaa                                                  1940
```

<210> SEQ ID NO 2
<211> LENGTH: 498
<212> TYPE: PRT
<213> ORGANISM: Mus musculus

<400> SEQUENCE: 2

```
Met Gly Leu Leu Val Ser Arg Val Leu Arg Cys Arg Asp Ser Ser Leu
1               5                   10                  15

Leu Glu Pro Gln Pro Glu Ala Ile Ala Gly Ala Ser Tyr Ile Pro Gly
            20                  25                  30

Ser Arg Lys Arg Lys Arg Asn Ser Leu Glu Glu Leu Ala Thr Ser Ser
        35                  40                  45

Asn Val His Gly Pro Gln Asn Gln Gly Met Tyr Pro His Gln Val Leu
    50                  55                  60

Asn Tyr Ile Tyr Trp Lys Arg Val Lys Ile Ser Ser Asn Asp Ala Tyr
65                  70                  75                  80

Gln Asn Leu Phe Leu Asp Gly His Asp Ser Asp Ile Lys Leu Arg Ala
                85                  90                  95

Leu Gly Arg Thr Trp Cys Leu His Lys Val Phe Leu Cys Gln Ser Gly
            100                 105                 110

Tyr Phe Ala Asn Ile Leu Lys Gly Thr Trp Arg Glu Ser His His Gly
        115                 120                 125

Val Ile Asn Leu Ile Ile Lys Asn Glu Asp Ile Asp Thr Arg Ser Leu
    130                 135                 140

His Phe Val Phe Gly Ala Leu Tyr Thr Asp Ala Asp Leu Ser Ile Thr
145                 150                 155                 160

Pro Leu Glu Val Pro Gln Val Leu Ala Ala Cys Leu Leu Arg Val
                165                 170                 175

Asp Arg Val Ile Gln Gln Cys Glu Gly Ile Met Lys Glu Thr Ile Asn
            180                 185                 190

Arg Asn Thr Val Cys Ser Tyr Tyr Leu Ala Ala Glu Thr Tyr Arg Leu
        195                 200                 205

Lys Ala Val Lys Thr Arg Cys Phe Glu Trp Leu Leu Cys Asn Leu Met
    210                 215                 220

Val His Pro Ser Val Ala Leu Tyr Lys Glu Val Asp Met Lys Leu Met
225                 230                 235                 240

Tyr Leu Leu Ala Leu Ser Ser Asp Leu Leu Val Met Gln Lys Glu Ile
```

```
                    245                 250                 255
Asp Val Tyr Thr Thr Leu Lys Ile Trp Met Ile Leu Tyr Leu Asn Pro
                260                 265                 270
Cys Trp Asn Gly Thr Met Lys Gln Leu Leu Gln His Ala Asn Asn Trp
            275                 280                 285
Leu Ser Thr His Met Ala Tyr Ile Asp Asn Ile Ser Phe Leu Glu Ser
        290                 295                 300
Glu Gly Leu Ile Phe Gln Pro Val Phe Lys Leu Arg Phe Gln
305                 310                 315                 320
His Ile Ile Cys Asp Leu Thr Ser Thr Ile Leu Glu Gln Asp Arg
                325                 330                 335
Leu Ile Pro Met Ala Trp Leu Ser Pro Ile Tyr Lys Gln Gln Trp Leu
                340                 345                 350
Thr Leu Leu Arg Thr Gln Glu Tyr Gly Val Ile Gly Pro Gln Val Ile
            355                 360                 365
Asn Glu Gln Glu Leu Glu Cys Thr Met Arg Cys Gly Thr Met Ile
        370                 375                 380
Pro Lys Asp Gly Arg Tyr Thr Trp Lys Trp Ser Val Gly Arg Leu Gly
385                 390                 395                 400
Phe Pro Leu Arg Val Thr Phe Thr Arg Gln Cys Val Ile Leu Arg Gln
                405                 410                 415
Arg Cys Gln Arg Cys Asp Gly Ser Ala Cys His Asn His Ile Arg Asn
                420                 425                 430
Val Ile Phe Arg Ile Thr Leu Val Cys Phe Asp Ser Asn Lys Arg Val
                435                 440                 445
Thr Phe Arg Lys Thr Thr Gly Tyr Lys Ile Leu Thr Phe Glu Tyr Asn
            450                 455                 460
Glu Gln Ile Val Met Lys Leu Asp Ser Asp Val Leu Thr Phe Pro
465                 470                 475                 480
Met Cys Ile Phe Cys Asn Phe Leu Phe Val Asn Leu Gly Asn Ala Glu
                485                 490                 495
Asn Lys

<210> SEQ ID NO 3
<211> LENGTH: 13
<212> TYPE: DNA
<213> ORGANISM: Artificial sequence
<220> FEATURE:
<223> OTHER INFORMATION: PCR primer AP6

<400> SEQUENCE: 3
aagcttgcac cat                                                           13

<210> SEQ ID NO 4
<211> LENGTH: 20
<212> TYPE: DNA
<213> ORGANISM: Artificial sequence
<220> FEATURE:
<223> OTHER INFORMATION: PCR primer HT15-C

<400> SEQUENCE: 4
aagctttttt tttttttttc                                                    20

<210> SEQ ID NO 5
<211> LENGTH: 26
<212> TYPE: DNA
<213> ORGANISM: Artificial sequence
<220> FEATURE:
```

```
<223> OTHER INFORMATION: PCR primer

<400> SEQUENCE: 5
ctgggaagaa catggtgttt acacaa                                              26

<210> SEQ ID NO 6
<211> LENGTH: 24
<212> TYPE: DNA
<213> ORGANISM: Artificial sequence
<220> FEATURE:
<223> OTHER INFORMATION: PCR primer

<400> SEQUENCE: 6
taaagtgcca cacttgatgt acca                                                24

<210> SEQ ID NO 7
<211> LENGTH: 24
<212> TYPE: DNA
<213> ORGANISM: Artificial sequence
<220> FEATURE:
<223> OTHER INFORMATION: PCR primer

<400> SEQUENCE: 7
aatgcctcaa ccaagaagcc tctg                                                24
```

TESTIS-SPECIFIC GENE

BACKGROUND OF THE INVENTION

1. Field of the Invention

This invention relates to a testis-specific gene, and particularly relates to a gene which is located on the X-chromosome and is specifically expressed in haploid cells of the testis, and relates to uses thereof.

2. Description of Related Art

Various genes, such as protamine, have already been reported as genes which are specifically expressed in haploid cells of the testis. However, among these genes, only fsc1 is known as a gene which is located on the X-chromosome and is specifically expressed in haploid cells of the testis.

In order to carry out chromosomal manipulations of the livestock, gene diagnostics or gene therapy for infertility due to sperm dysplasia, or the like, by means of artificially manipulating gene expression in the testis, or introducing a gene or a recombinant, which can be specifically expressed in haploid cells, it is indispensable that a gene which is located on a sex chromosome and is specifically expressed in the haploid cells of the testis be isolated and be utilized.

SUMMARY OF THE INVENTION

This invention provides a gene specifically expressed in haploid cells of the testis.

This invention provides a gene, which is located on the X-chromosome of a mammal, is specifically expressed in haploid cells of the testis, and encodes an amino acid sequence having a homology of at least 25% with an amino acid sequence encoded by drosophila gcl gene.

The mammal can be selected from the group including mouse, human, and cattle.

This invention also provides a DNA which can hybridize, under stringent conditions, with a DNA including the base sequence in SEQ ID NO: 1 or a DNA sequence containing substitution, deletion, and/or addition of one or more nucleotides in a base sequence in SEQ ID NO: 1.

The invention further provides a protein including an amino acid sequence in SEQ ID NO: 2, or a protein including an amino acid sequence containing substitution, deletion, and/or addition of one or more amino acid residues in the amino acid sequence in SEQ ID NO: 2. The invention further provides an RNA transcribed from the aforementioned DNA.

The invention further provides a method of gene diagnosis by using a base sequence in SEQ ID NO: 1. The invention further provides a method of discrimination of sex by using a base sequence in SEQ ID NO: 1. The invention further provides a method of separation of sperm by using a base sequence in SEQ ID NO: 1 or by using an amino acid sequence in SEQ ID NO: 2. The invention further provides a method of infertility treatment by using a base sequence in SEQ ID NO: 1 or by using an amino acid sequence in SEQ ID NO: 2. The invention further provides a method of chromosomal manipulation by using a base sequence in SEQ ID NO: 1.

BRIEF DESCRIPTION OF THE DRAWINGS

FIG. 1A shows a result of differential display analysis using a DNA sequencer and FIG. 1B shows a result of differential display analysis using preparative polyacrylamide gel electrophoresis.

FIG. 2 shows a base sequence of cDNA of murine gclh (mgclh) gene (SEQ ID NO:1).

FIG. 3 shows an amino acid sequence (SEQ ID NO: 2) encoded by the mgclh gene.

DETAILED DESCRIPTION OF THE INVENTION

Figure 1A:
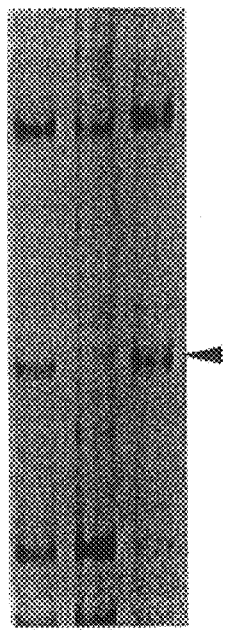
FIGS. 1A and 1B show photographs of electrophoretic profiles analyzed by differential display of the genes specifically expressed in mature murine testis and isolated round spermatids.

In the first stage of the formation of drosophila germ cells, special cells called as pole cells containing pole plasm localizing at the posterior pole of a fertilized egg are formed. The gcl gene is indispensable for the formation of the pole cells, and gcl-mRNA transcribed from the gcl gene is localized in the pole plasm. When the expression of gcl protein is suppressed, the formation of the germ cells is known to be significantly inhibited. The base sequence of the drosophila gcl gene and the amino acid sequence encoded by the gene are disclosed by Jongen, et al., in Cell 70, 569-584(1992); "The germ cell-less gene product: a posteriorly localized component necessary for germ cell development in Drosophila".

A gene according to this invention is a drosophila gcl gene homolog obtained from a mammal, located on the X-chromosome of a mammal, and is specifically expressed in the haploid cells of the testis, that is, in germ cells. The gene according to this invention has an amino acid sequence homology of at least 25% with the amino acid sequence encoded by drosophila gcl (germ cell-less) gene.

In this specification, the species of mammal are not limited, and include all species generally understood as being mammalian. Particularly useful species of mammal selected from livestock include the cattle, horse, sheep, goat, rabbit, pig, and the like.

The gene according to this invention and homologs thereof can be prepared as DNA hybridized with DNA containing the base sequence presented in SEQ ID NO: 1 under stringent conditions, by means of screening a cDNA or genome library using a probe selected according to the method described, for example, Sambrook, et al., in Molecular Cloning: A Laboratory Manual (New York, Cold Spring Harbor Laboratory Press, 1989). Alternatively, the PCR method described by Dieffenbach, et al., in PCR Primer: A Laboratory Manual (Cold Spring Harbor Laboratory Press, 1995) may be used for preparing the gene and the homologs.

The amino acid homology can be analyzed by means of a publically available computer software, such as BLAST, ALIGN, or Megalign (DNA STAR), according to a standard technique for those skilled in the art. A preferable software alignment program is BLAST. Those skilled in the art can decide suitable parameters for measuring alignment including an algorithm required for obtaining the alignment covering the longest length to be compared.

The "stringent conditions" means to wash under low salt and high temperature conditions, such as is provided by 0.015 M sodium chloride/0.0015 M sodium citrate/0.1% sodium dodecyl sulfate at 50° C., for example (1), or to use, during hybridization at 42° C., a denaturant such as 50% (vol/vol) formamide including 50 nM sodium phosphate (pH 6.5) containing 0.1% bovine serum albumin/0.1% Ficol/0.1% polyvinyl pyrrolidone/750 mM sodium chloride and 75 mM sodium citrate, for example (2). Alternatively, the "stringent conditions" means to hybridize at 42° C. using, as a hybridization buffer, a solution containing 50% formamide, 5×SSC (0.75 M sodium chloride, 0.075 M sodium citrate), 50 mM sodium phosphate (pH 6.8), 0.1% sodium pyrophosphate, 5×Denhardt regent, sonicated salmon sperm DNA (50 µg/ml), 0.1% SDS, and 10% dextran sulfate, followed by washing with 0.2×SSC and 0.1% SDS at 42° C. Alternatively, the "stringent conditions" means to hybridize at 55° C. using, as a hybridization buffer, a solution containing 50% formamide, 2×SSC, and 10% dextran sulfate, followed by highly stringent washing with 0.1×SSC containing EDTA at 55° C.

Or alternatively, moderately stringent conditions may be selected (see the aforementioned reference by Sambrook, et al.). The "moderately stringent conditions" means to incubate overnight at 37° C. in a solution containing 20% formamide, 5×SSC (150 mM sodium chloride, 15 mM trisodium citrate), 50 mM sodium phosphate (pH 7.6), 5×Denhardt regent, 10% dextran sulfate, and denatured sonicated salmon sperm DNA (20 mg/mL), followed by washing a filter with 1×SSC at 37 to 50° C., for example.

A protein according to this invention includes an amino acid sequence in SEQ ID NO: 2, or an amino acid sequence containing substitution, deletion, and/or addition of one or more amino acid residues in the amino acid sequence in SEQ ID NO: 2. The protein can be prepared by isolating from natural proteins, synthesizing, or using DNA containing the base sequence in SEQ ID NO: 1, according to a standard recombination technique (see the aforementioned reference by Sambrook, et al.).

This invention will be explained in detail, by way of examples. However, since uses of the entirety or part of the mgclh gene represented by the aforementioned base sequence or the aforementioned amino acid sequence of this invention, and of gene homologs, cDNA, RNA, and protein thereof, have an enormous range of possibilities, this invention is not limited to the following examples.

EXAMPLES

1) Identification of a Gene by Means of Differential Display Method

A fluorescent mRNA Differential Display (referred to as DD, hereinafter) method was used to analyze or isolate a gene specifically expressed in haploid cells of the murine testis. That is, testes were extirpated from a mature male mouse having testes with haploid cells or an immature male mouse (17 days old) in which the testes did not have haploid cells, from which total RNA was prepared according to the AGPC (Alkaline Guanidine Phenol Choloforn) method. In contrast, round spermatids (haploid cells) were isolated from the testes of a mature male mouse according to an elutriation method, from which total RNA was prepared in the same manner as previously set forth. In preparing total RNA, a trace of DNA included in samples was removed by DNase treatment.

The DD method for analyzing was basically carried out according to a manual by the Gene Hunter Co. First, each of the aforementioned total RNA was subjected to reverse transcription to prepare cDNA. Then, each of the prepared cDNA (corresponding to 0.02 µg of RNA) was subjected, as a template, to PCR, using an upstream arbitrary primer (AP6, 5'-AAGCTTGCACCAT-3') (SEQ ID NO: 3) and a downstream anchor primer modified by fluorescent labels with IRD (HTI 5-C, 5'-AAGCTTTTTTTTTTTTTTC-3') (SEQ ID NO: 4). The PCR was carried out by means of a PC-9600 type thermal cycler manufactured by Perkin Elmer Co. under conditions including: 1 cycle containing steps of denaturing at 94° C. for 2 minutes, annealing at 40° C. for 5 minutes, and extension at 72° C. for 5 minutes; 29 cycles containing steps of denaturing at 94° C. for 15 seconds, annealing at 40° C. for 5 minutes, and extension at 72° C. for 1 minute; and 1 cycle containing a step of subsequent heating at 72° C. for 5 minutes. DNA fragments amplified by the PCR were analyzed by means of a DNA sequencer (DNA 4000) manufactured by LiCor Co.

FIG. 1A shows results indicating electrophoretic profiles of the DNA fragments from the mature murine testes, the immature murine testes, and the round spermnatids, which were analyzed by the aforementioned DNA sequencer. In the electrophoretic profiles of the DNA fragments from the mature murine testes and the round spermatids, a common fluorescent band was detected, which was not detected in the electrophoretic profiles of the DNA fragments from the immature murine testes. The common band was supposed to be DNA fragments from the gene specifically expressed in haploid cells of the murine testis (which is indicated by an arrow in FIG. 1A). The length of the fragments was estimated to be approximately 760 bp.

Figure 1B:
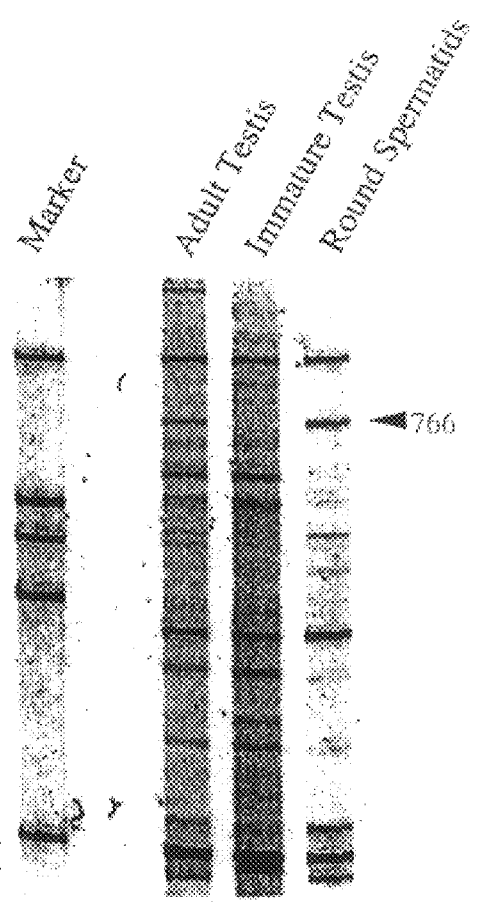

Then, the DD method for isolating was carried out using the PCR conditions similar to that of the DD method for analyzing except for using an anchor primer modified by fluorescent labels with Texas Red instead of the anchor primer modified by fluorescent labels with IRD. FIG. 1B shows results indicating electrophoretic profiles of obtained DNA fragments which were subjected to 4% polyacrylamide gel electrophoresis containing 7M urea, followed by analyzing by means of a fluorescent image scanner (FMBIO II) manufactured by TAKARA Co., LTD. As is obvious from FIG. 1B, a band showing the DNA fragments from the gene specifically expressed in haploid cells of the murine testis was easily identified. Then, the band was cut from the gel with reference to the mobility of a marker DNA, followed by extracting the DNA fragments according to a conventional method. The extracted DNA fragments were reamplified by the PCR, and were then subjected to the aforementioned polyacrylamide gel electrophoresis so as to ensure that the reamplifiled DNA fragments have the same mobility as that of the extracted DNA fragment. The rearnplified DNA fragments were subcloned by using a TA cloning kit, and were sequenced according to a conventional method. As a result of determining base sequence of the DNA fragments, the DNA fragments were revealed to have a length of 766 nucleotides. Moreover, the DNA fragments were revealed to be a novel gene sharing a high degree of homology with the drosophila germ cell-less (gcl) gene, as a result of conducting a homology search based on the base sequence of the DNA fragments by means of BLAST. Therefore, the gene was termed "mgclh" gene meaning murine gcl gene specifically expressed in haploid testis cells.

2) Cloning of cDNA and Determination of Base Sequence of the cDNA

In order to determine the full length base sequence of the cDNA of the mgclh gene and to estimate the amino acid sequence of a protein encoded by the mgclh gene, a cDNA library generated from round spennatids of BALB/c mouse and constructed in plasmid vector pUC118 was screened using the DNA fragments as a probe. That is, colony hybridization was carried out by hybridizing DNA immobilized on nylon membranes from 50,000 colonies to a $^{32}$P-labeled probe prepared from the DNA fragments under stringent conditions (at 42° C. for 16 hours in a solution containing 50% formamide, 10% dextran sulfate, 1% SDS, SxDenhard reagent, and 2×SSC). When the hybridization was completed, the nylon membranes were washed four times under stringent conditions (at 65° C. for 15 minutes in a solution containing 0.1% SDS and 1×SSC), and were then visualized by autoradiography to detect spots by exposing X-ray film. As a result of the screening, 7 independent clones were isolated. When cDNAs extracted from the clones were sequenced by a conventional method, they were revealed to be cDNA containing the base sequence shown in FIG. 2 (SEQ ID NO: 1) and encoding the amino acid sequence shown in FIG. 3 (SEQ ID NO: 2). Moreover, 6 kinds of clones transcribed from the DNA fragments were identified in addition to the aforementioned clone, which were polymorphistic genes each having a base sequence including substitution of a few or more nucleotides in the base sequence shown in FIG. 2 and each encoding a protein having an amino acid sequence including substitution of 1, 2, 3, 4, 5, or 9 amino acid residues in the amino acid sequence shown in FIG. 3. That is, when each of the amino acid sequence encoded by the 6 clones were compared with the amino acid sequence shown in FIG. 3, multiple substitutions of amino acid residues were recognized, for example, in which the 10th amino acid R was substituted with S, the 23rd amino acid A was substituted with G, the 32nd amino acid G was substituted with V, the 76th amino acid S was substituted with Y, the 115th amino acid A was substituted with T, the 120th amino acid G was substituted with D, the 182th amino acid Q was substituted with K, the 267th amino acid F was substituted with 1, the 278th amino acid M was substituted with T, the 325th amino acid D was substituted with N, the 464th amino acid N was substituted with K, the 465th amino acid E was substituted with Q, etc. In contrast, when homology analysis using the amino acid sequence shown in FIG. 3 was conducted, the amino acid sequence shown in FIG. 3 (mgclh) was revealed to have a homology of 25%/43% [identity (%)/similarity (%)] with drosophila gcl (dgcl) and a homology of 45%/61% with murine dip (mdip).

3) Cloning of the mgclh Gene and Determination of Base sequence of the mgclh Gene In order to determine the full length base sequence of the mgclh gene, 5 independent clones were isolated by screening a BAC library of genomic DNA from BALB/c mouse. Then, the isolated genomic DNA was amplified by the PCR using various primers constructed based on the base sequence of the aforementioned cDNA. The structure of the genomic DNA was estimated from the length of the amplified DNA fragments. As the result, it was revealed that the mgclh gene is a rare gene which does not contain any introns in coding regions (that is, it is intronless), and that has a genetic polymorphism.

4) Cloning of cDNA from Other Mammals and Determination of Base Sequences Thereof.

cDNAs of gclh genes (gene homologs) from human and cattle were respectively isolated by means of RT-PCR, and the base sequences thereof were determined in a similar manner as previously set forth.

The RT-PCR was conducted as follows. First, RT (reverse transcription) reaction was conducted by using, as a template, 0.125 ng of human testis poly(A)+RNA (manufactured by Clontech Co.), or alternatively, by using, as a template, 1.25 ng of bovine testis total RNA prepared from mature bovine testis according to the aforementioned method. Then, a degenerating PCR was conducted by using a sense primer (5'-CTGGGAAGAACATGGTGTTTACACAA-3') (SEQ ID NO: 5) and an antisense primer (5'-TAAAGTGCCACACTTGATGTACCA-3') (SEQ ID NO: 6), which were constructed based on the base sequence of the murine gclh (mgclh) gene, under conditions including: 1 cycle containing steps of denaturing at 94° C. for 2 minutes, annealing at 40° C. for 5 minutes, and extension at 72° C. for 5 minutes; 34 cycles containing steps of denaturing at 94° C. for 15 seconds, annealing at 40° C. for 2 minutes, and extension at 72° C. for 1 minute; and 1 cycle containing a step of subsequent heating at 72° C. for 5 minutes. When DNA fragments amplified by the degenerating PCR were subjected to agarose gel electrophoresis according to a conventional method, DNA fragments having the same length as that from the mouse described above were observed in both electrophoretic profiles obtained from human and cattle.

The DNA fragments were cut from the gel, were subcloned with a TA vector, and were then sequenced. As a result of the sequence analysis, the base sequences from human and cattle were significantly similar to each other.

Next, after the aforementioned RT reaction using, as a template, the human testis poly(A)+RNA or the bovine testis total RNA, the ordinary PCR was conducted by using a sense primer (5'-AATGCCTCAACCAAGAAGCCTCTG-3') (SEQ ID NO: 7) and an antisense primer (5'-TAAAGTGCCACACTTGATGTACCA-3') (SEQ ID NO: 6), between which a larger region of the base sequence of the mgclh gene was contained, under conditions including: 1 cycle containing a step of denaturing at 94° C. for 5 minutes; 30 cycles containing steps of denaturing at 94° C. for 20 seconds, annealing at 58° C. for 30 seconds, and extension at 72° C. for 2 minutes; and 1 cycle containing a step of subsequent heating at 72° C. for 5 minutes. After the agarose gel electrophoresis, the amplified DNA fragments (747 bp) were cut from the gel, were subcloned with a TA vector, and were then sequenced. As a result, it was revealed that each of the amplified DNA fragments obtained from human (hgclh) and cattle (bgclh) had a base sequence significantly similar to that of mouse (mgclh), and had multiple gene copies. Moreover, polymorphic genes each having a base sequence including substitution of multiple nucleotides in the base sequence of the mgclh cDNA were recognized. Furthermore, it was revealed that the hgclh, bgclh, and mgclh genes were highly conserved among species, and the conservation was sufficient to encode proteins having an amino acid sequence homology of 95 to 99% with each other.

5) Analysis of the expression of the gene by means of Northern blot analysis

Figure 4A:
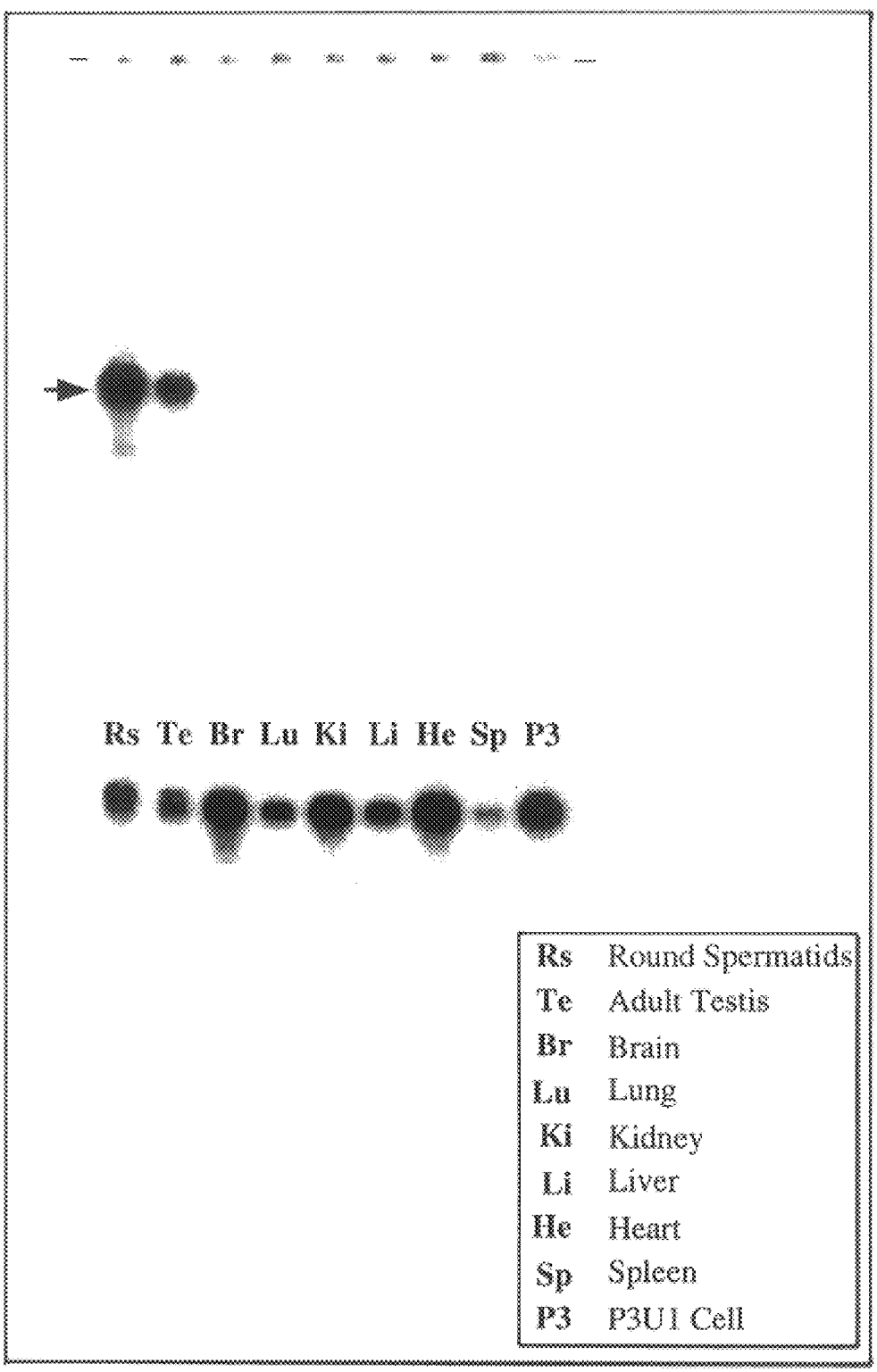
FIG. 4A shows a photograph of an electrophoretic profile analyzed by Northern blot, which indicates the expression of the mgclh gene in various tissues and cells.

Northern blot analysis for estimating the expression of the mgclh gene in various tissues was carried out in order to confirm that the mgclh gene was specifically expressed in haploid cells. That is, each RNA was prepared from, according to the aforementioned AGPC method, various tissues such as testis, brain, lung, kidney, liver, heart, and spleen, round spermatids, and P3U 1 cells. Then, 5 μg of each prepared RNA was electrophoresed in a fortnalin gel. After the electrophoresis, the electrophoresed RNA was transferred to a nylon membrane, followed by carrying out hybridization reaction using the aforementioned $^{32}$P-labeled mgclh DNA fragments as a probe. At this time, $^{32}$P-labeled G3PDH DNA fragments, which was known to be expressed in all tissues, was used as a positive control probe. The upper part of FIG. 4A shows results indicating the expression of the mgclh gene, and the lower part of the FIG. 4A shows results indicating that the G3PDH gene was expressed in all tested tissues and cells. As is obvious from the results of FIG. 4A, mRNA transcribed from the mgclh gene was approximately 2.1 kb in length, was specifically expressed in testis, and was strongly expressed in haploid round spermatids.

Figure 4B:
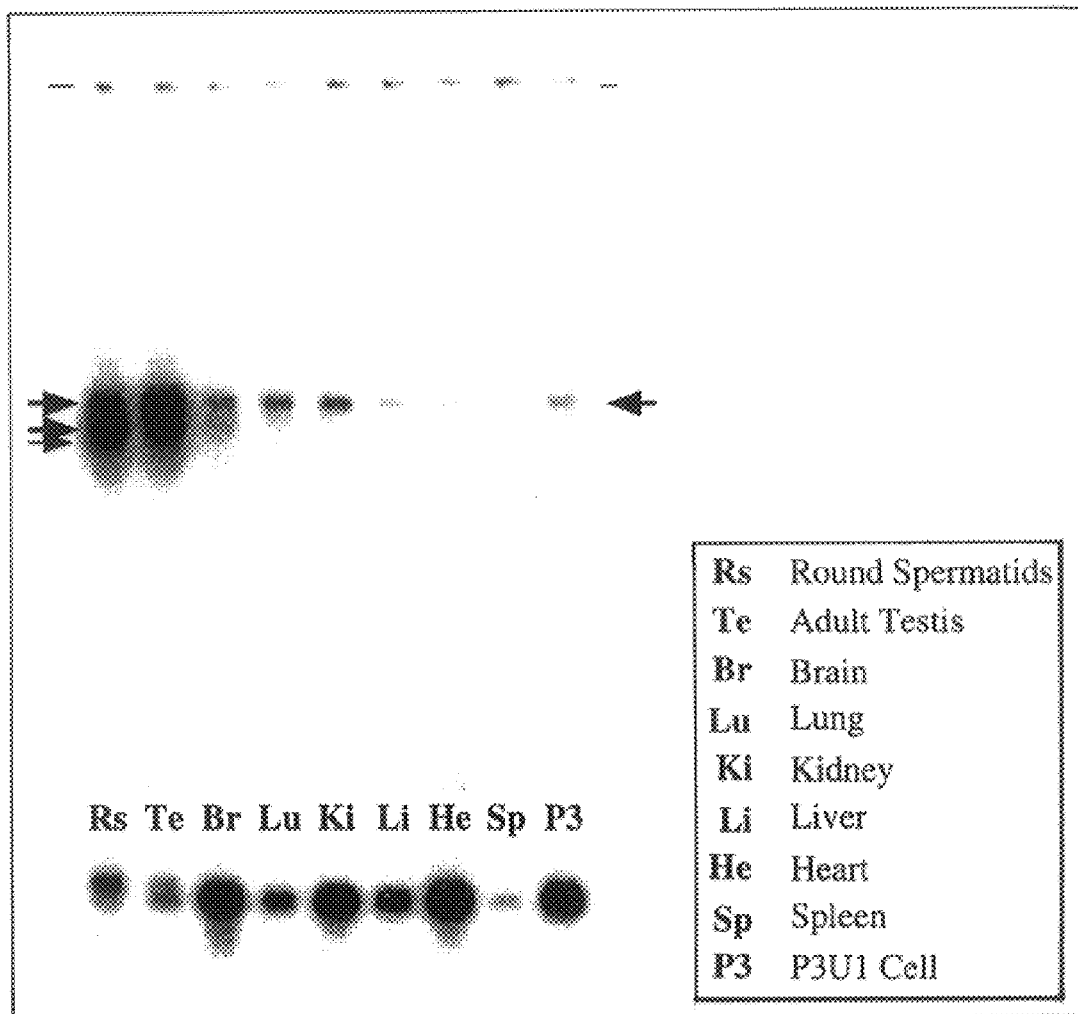
FIG. 4B shows a photograph of an electrophoretic profile analyzed by Northern blot of the expression of the mdip gene in various tissues and cells.

Moreover, the hybridization reaction was carried out in a manner similar to that of FIG. 4A except that $^{32}$P-labeled mdip DNA fragments, which was cloned from mouse and had a high homology with the drosophila gcl DNA, were used instead of the $^{32}$P-labeled mgclh DNA fragments. The upper part of FIG. 4B shows results indicating the expression of the mdip gene, and the lower part of the FIG. 4B shows results indicating that the G3PDH gene was expressed in all tested tissues and cells. As is obvious from the results of FIG. 4B, although the mdip gene was strongly expressed in testis and round spermatids, and was transcribed into mRNA having a length similar to that of the mgclh mRNA, the mdip gene was expressed in all tested tissues and cells. Thus, it was revealed that the expression manners of the mgclh and the mdip were quite different from each other.

Figure 5:
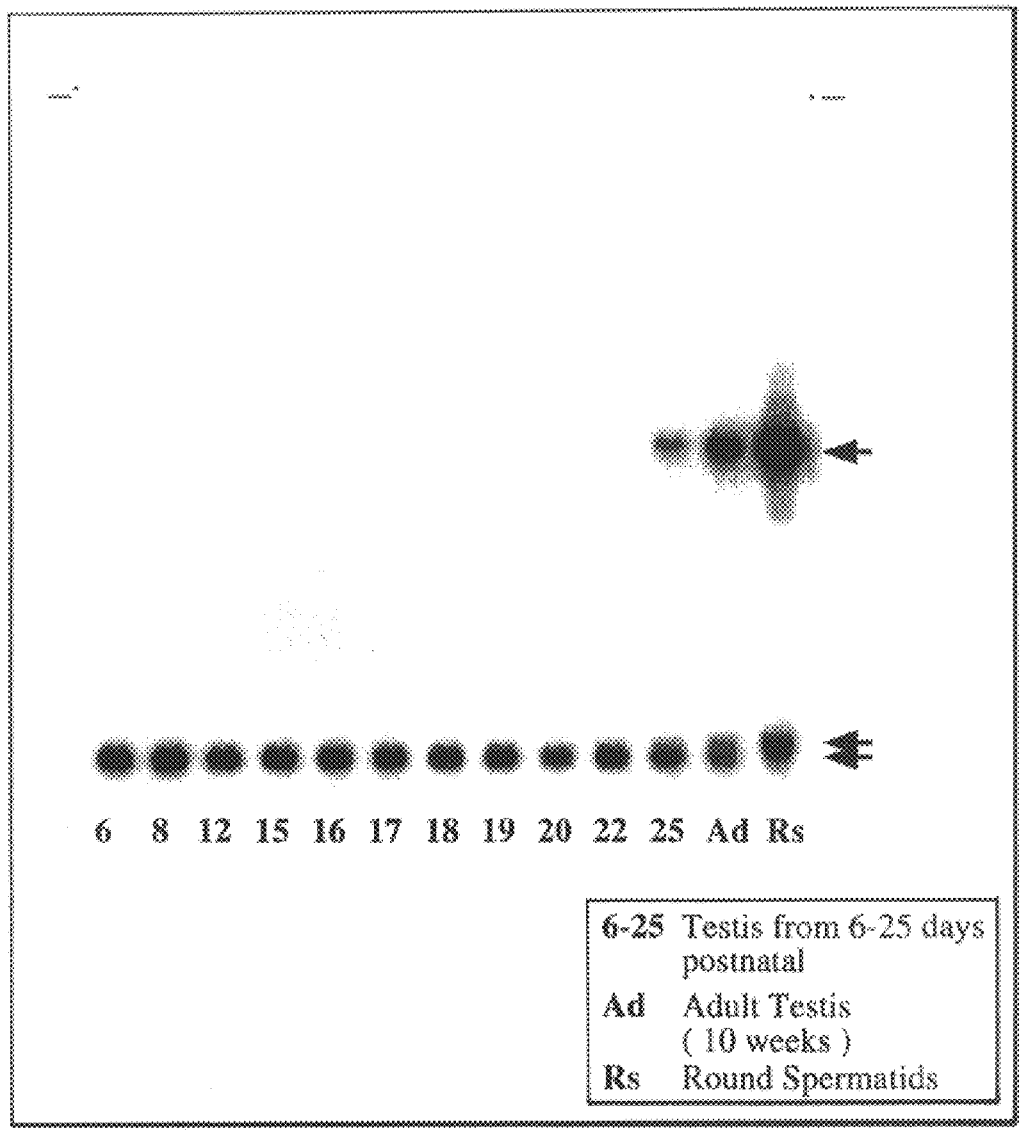
FIG. 5 shows a photograph of an electrophoretic profile analyzed by Northern blot, which indicates the expression of the mgclh gene in various spermatogenic stages in murine testis or isolated round spermatids.

In order to estimate the expression of the mgclh gene in various spermatogenic stages, RNA was prepared from each testis and isolated round spermatids of young (immature) mice 6 to 25 days old and a mature mouse 10 weeks old, each of which was used for Northern blot analysis. FIG. 5 shows results of the Northern blot analysis. As is clear from FIG. 5, the mgclh gene was expressed from 22 days after birth, and was strongly expressed in isolated round spermatids. In view of the fact that the testis of the mouse had normally matured, that is, the formation of sperm had normally started, 20 days after birth, the mgclh gene was supposed to be specifically expressed in haploid cells and to play an important role in morphogenesis of sperm.

Figure 6A:
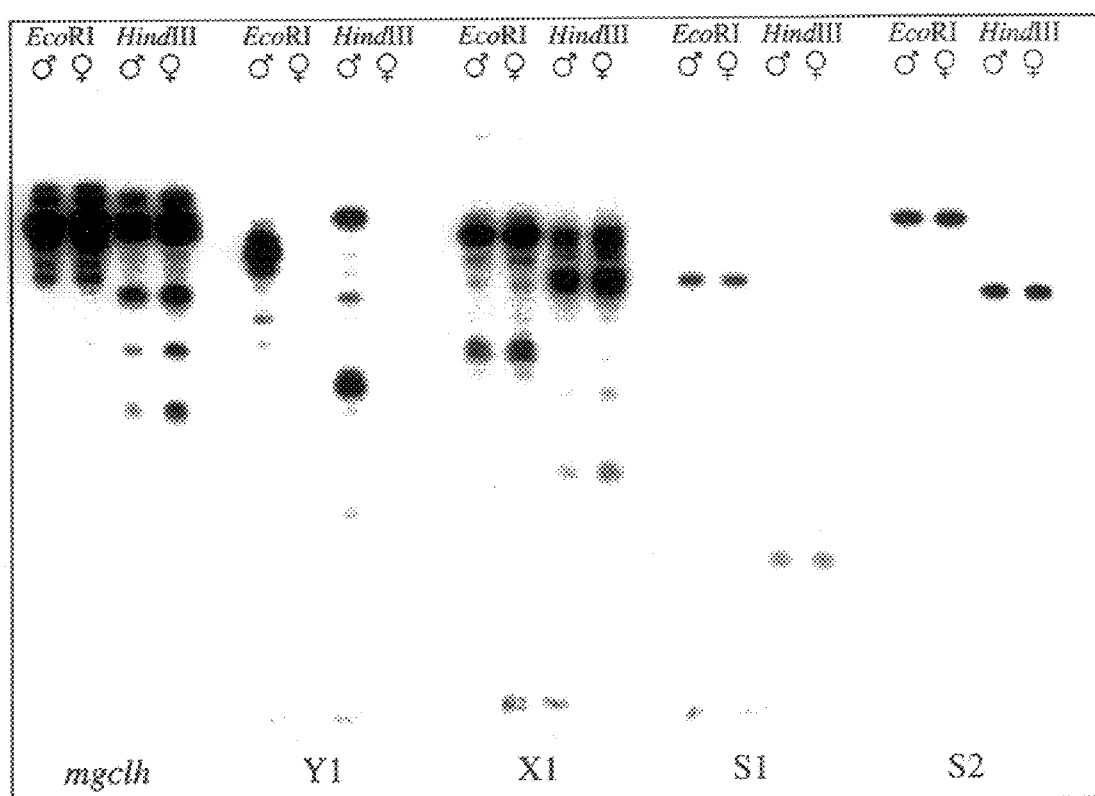
FIG. 6A shows a photograph of an electrophoretic profile analyzed by Southern blot, which indicates the expression of the mgclh gene using murine genomic DNA digested by Eco RI and Hind III.
Figure 6B:
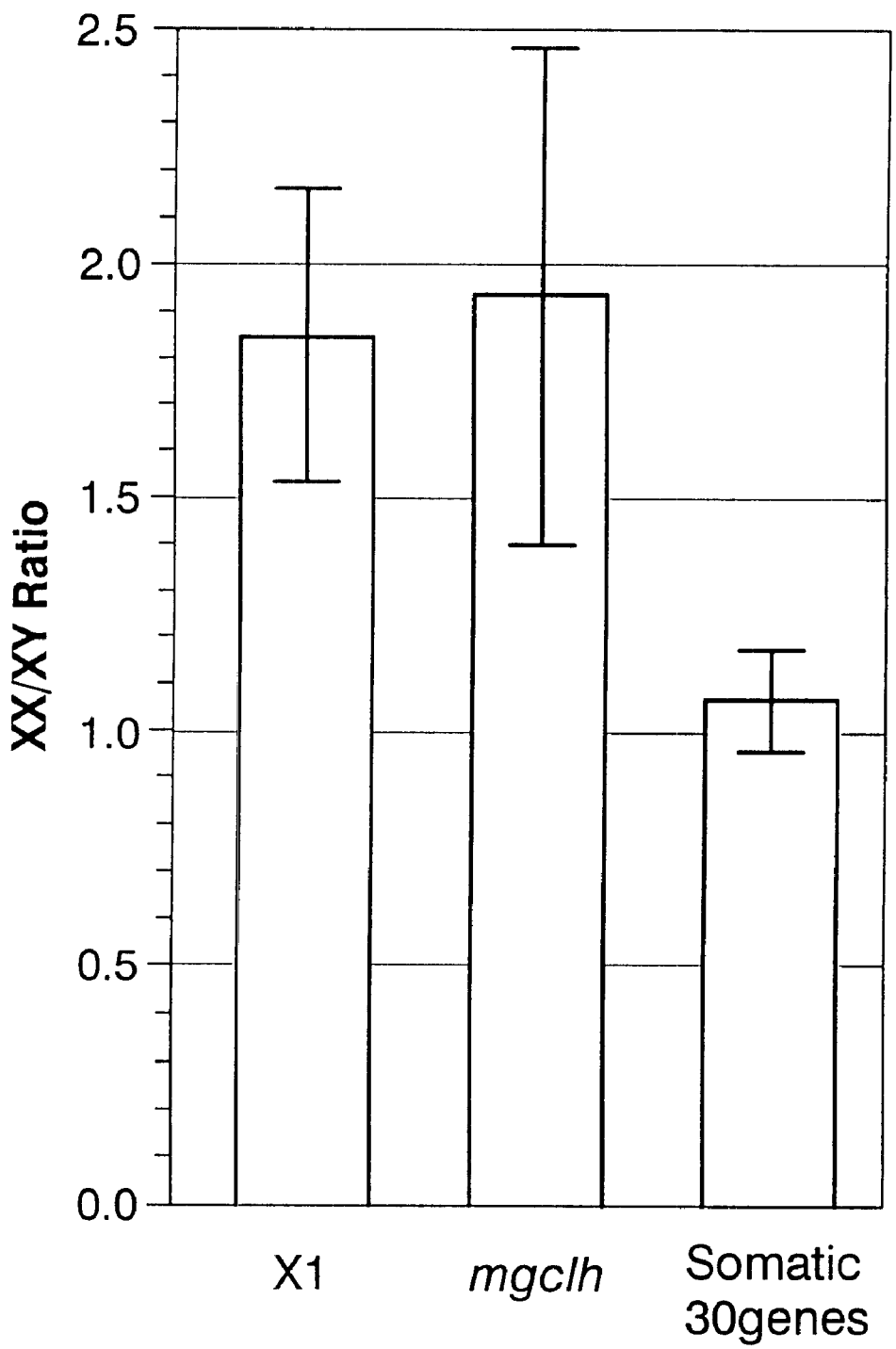
FIG. 6B is a graph indicating results of quantitative analysis according to the Southern blot analysis.

6) Comparison Between Genomic DNAs from Female and Male Mice by Means of Quantitative Southern Blot Analysis Quantitative Southern blot analysis was carried out in order to estimate quantitative differences between the mgclh genes in female and male murine genome, that is, to detect, from among autosomes, the X-chromosome, and the Y-chromosome, a chromosome on which the mgclh gene is located, and to determine whether that the mgclh gene exists in the genome as a single copy or in multiple copies. The quantitative Southern blot analysis was conducted according to the following procedures. Each genomic DNA was prepared from livers of a female and a male mouse according to a conventional method. Each DNA was digested by various pairs of restriction enzymes selected from Eco RI, Hind III, and Pst I. At this time, RNA included in each DNA sample was removed by means of RNase A treatment. Same amount of DNA samples were electrophoresed on 0.75% agarose gel in 1×TBE buffer, the electrophoresed DNA samples were transferred to a nylon membrane, followed by hybridization using the aforementioned $^{32}$P labeled mgclh DNA probe or the belowmentioned probe as a comparative probe for estimating the expression of various genes locating on autosomes, the X-chromosome, or the Y-chromosome. After autoradiography, radiation intensity of bands obtained in the autoradiogram was digitize by means of a scanner, from which the gene dosage was measured by means of a NIH-Image. FIG. 6A shows results of Southern blot analysis using murine genomic DNA digested by Eco RI and Hind III, and FIG. 6B is a graph showing results of the ratio of the gene dosage in the female genome to the gene dosage in the male genome (XX/XY).

As shown in FIG. 6A, when $^{32}$P labeled X1 DNA probe, which is located on the X-chromosome in multiple copies, was used as a comparative probe for hybridization, although multiple bands were detected in both the female and the male genome, the ratio of the X1 gene dosage in the female genome to the X1 gene dosage in the male genome (XX/XY) was approximately two. In contrast, when 32p labeled Y1 DNA probe, which is located on the Y-chromosome in multiple copies, was used as a comparative probe for hybridization, multiple bands were detected in only the male genome, and the ratio of the Y1 gene dosage in the female genome to the Y1 gene dosage in the male genome (XX/XY) was zero. Moreover, when 32P labeled S1 or S2 DNA probe, each of which is located on an autosome in a single copy, was used as a comparative probe for hybridization, only one common band was detected in both the female and the male genome, and the ratio of the S1 or S2 gene dosage in the female genome to the S1 or S2 gene dosage in the male genome (XX/XY) was approximately one. When the $^{32}$P labeled mgclh DNA probe was used for hybridization, although multiple bands were detected in both the female and the male genome, the ratio of the mgclh gene dosage in the female genome to the mgclh gene dosage in the male genome (XX/XY) was approximately two, and the ratio of the mgclh gene dosage in the female genome to the S1 or S2 gene dosage in the female genome was approximately ten. Thus, the mgclh gene was determined to be located on the X-chromosome in multiple copies of approximately ten copies.

7) Determination of Locus of the mgclh Gene on the Chromosome

Figure 7A:
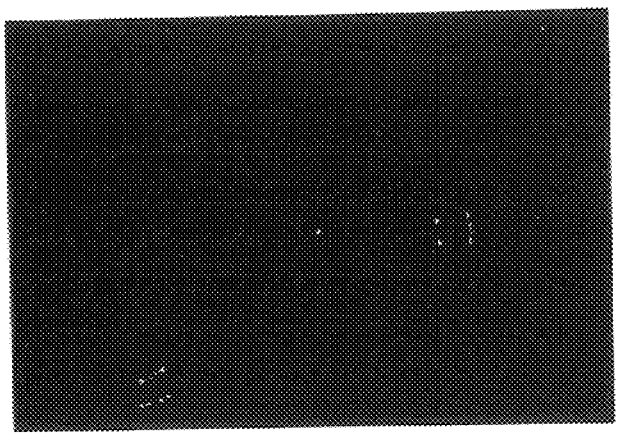
FIG. 7A shows a photograph indicating the location of the mgclh gene on the chromosome.
Figure 7B:
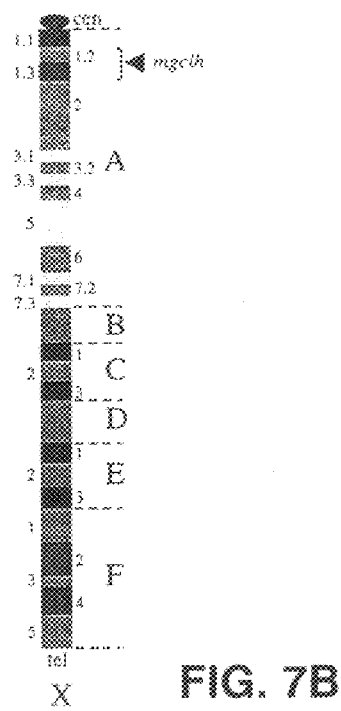
FIG. 7B is a map of murine X-chromosome indicating the locus of the mgclh gene.

Fluorescence in situ hybridization (FISH) analysis was carried out for clarifying the locus of the mgclh gene on the X-chromosome, and clarifying whether multiple copies of the mgclh gene were located forming a cluster on the X-chromosome or were dispersing on the X-chromosome. The FISH analysis was conducted according to the following procedures. First, the aforementioned five cloned DNAs from the BAC library, which include the mgclh DNA, were labeled with digoxigenin-dUTP (DIG-dUTP) according to a nick translation method to prepare probes. Each of the labeled probes was hybridized to chromosomes of murine fibroblast cells in metaphase together with sonicated total murine genomic DNA. After washing, followed by incubating with an anti-digoxigenin antibody labeled with fluorescein, and then by counter-staining with DAPI, specific signals were detected by using a fluorescence microscope. Since the specific signals were appeared to exist on a proximal region of the X-chromosome in a preliminary experiment, a probe confirmed to specifically react with telomere regions on the X-choromosome was also used together in the FISH analysis. FIG. 7A shows the obtained results of the FISH analysis. In FIG. 7A, two pairs of dots indicated by arrows represent signals from the probe specifically reacting with the telomere regions on the X-chromosome, and strong fluorescent signals near centromere regions on the X-chromosome, which are indicated by lines in FIG. 4A, represent specific signals indicating the locus of the mgclh gene. As a result of the FISH analysis using each of the probes prepared from the aforementioned five cloned DNAs, fluorescent signals indicating the locus of the each cloned DNA were detected on the same region as that shown in FIG. 7A, and were located near the borderline between heterochromatin and euchromatin, which was stained with DAPI. Thus, the mgclh gene was mapped to XA1.2-A1.3 region on a gene map shown in FIG. 7B.

8) Analysis of the Localization of the mgclh Gene in Testis by Means of in situ Hybridization Analysis The localization of the mgclh-mRNA in the testis containing sperm at various spermatogenic stages was analyzed by means of in situ hybridization analysis, in order to clarify that the mgclh gene was a gene specifically expressed in round spermatids in the testis. The in situ hybridization analysis was conducted according to the following procedures. First, a coding region of the mgclh gene was cloned into a Bluescript vector to produce a riboprobe. Then, sense and antisense digoxigenin-dUTP (DIG-UTP) labeled RNA probes were synthesized according to a standard in vitro transcription reaction using a T7 or T3 promoter. In contrast, fixed testes prepared by removing from male mice at various spermatogenic stages after perfusion fixation using a solution containing 4% paraformaldehyde and phosphate buffered saline, or by fixing in a Bouin's solution after removing testes from male mice in various spermatogenic stages were embedded into paraffin according to a standard method. The paraffin-embedded sample blocks were sliced into sections each having 6 μm thickness by means of a microtome.

The sections were mounted onto slides, and the slides were then dewaxed and were rehydrated. After the sections were digested with proteinase K, 100 ng of the antisense DIG-UTP labeled RNA probe in hybridization buffer were applied to the sections, and were then incubated at 42° C. for 14 to 16 hours. After washing, specific signals were detected using anti-DIG antibody -alkaline phosphatase conjugate and were developed with NBT/BCIP reagent. After counterstaining with safranine 0, detected signals were observed by using a microscope.

Figure 8:
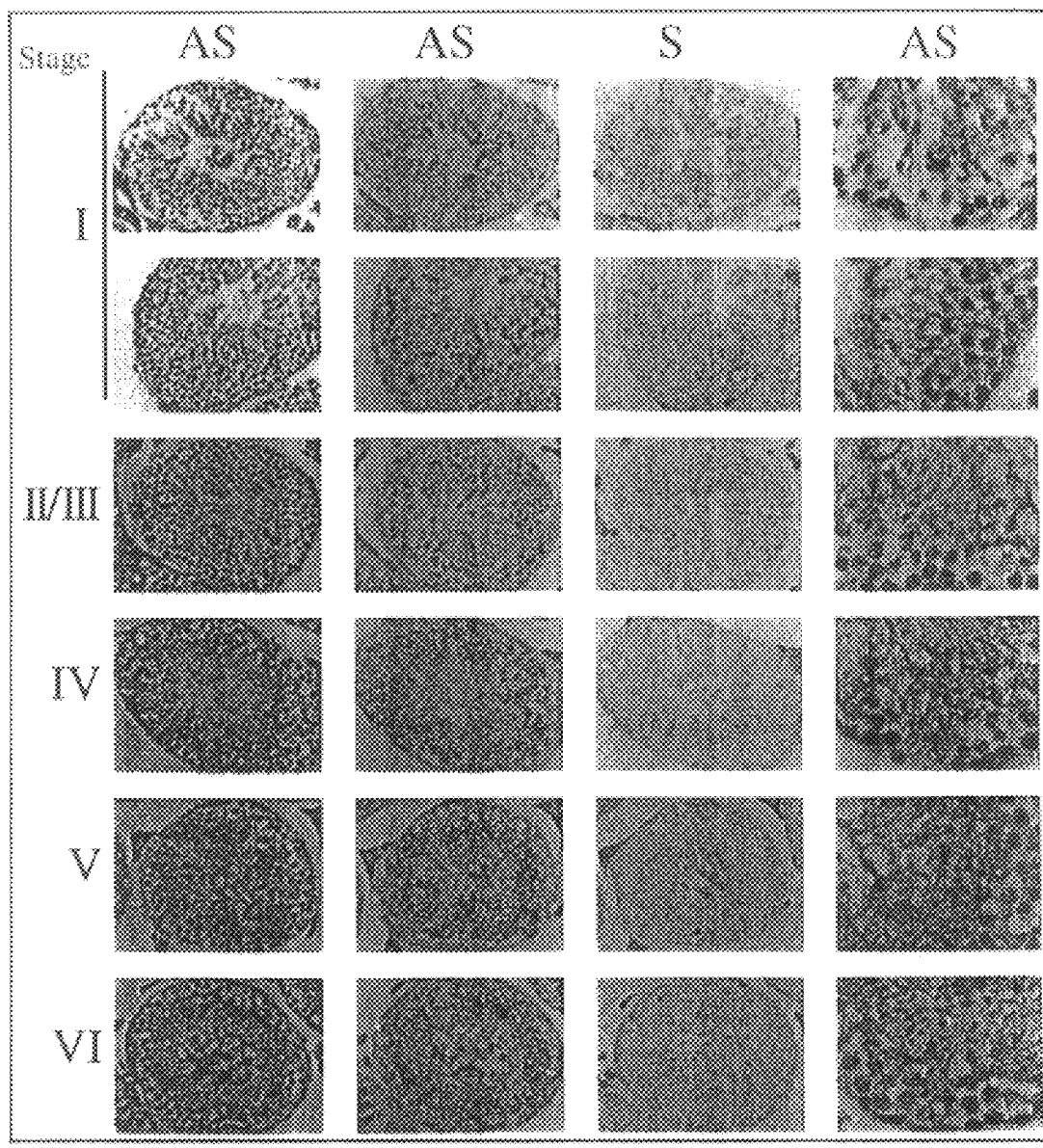
FIG. 8 shows photographs indicating the localization of the mgclh gene in various spermatogenic stages of the testis.
Figure 9:
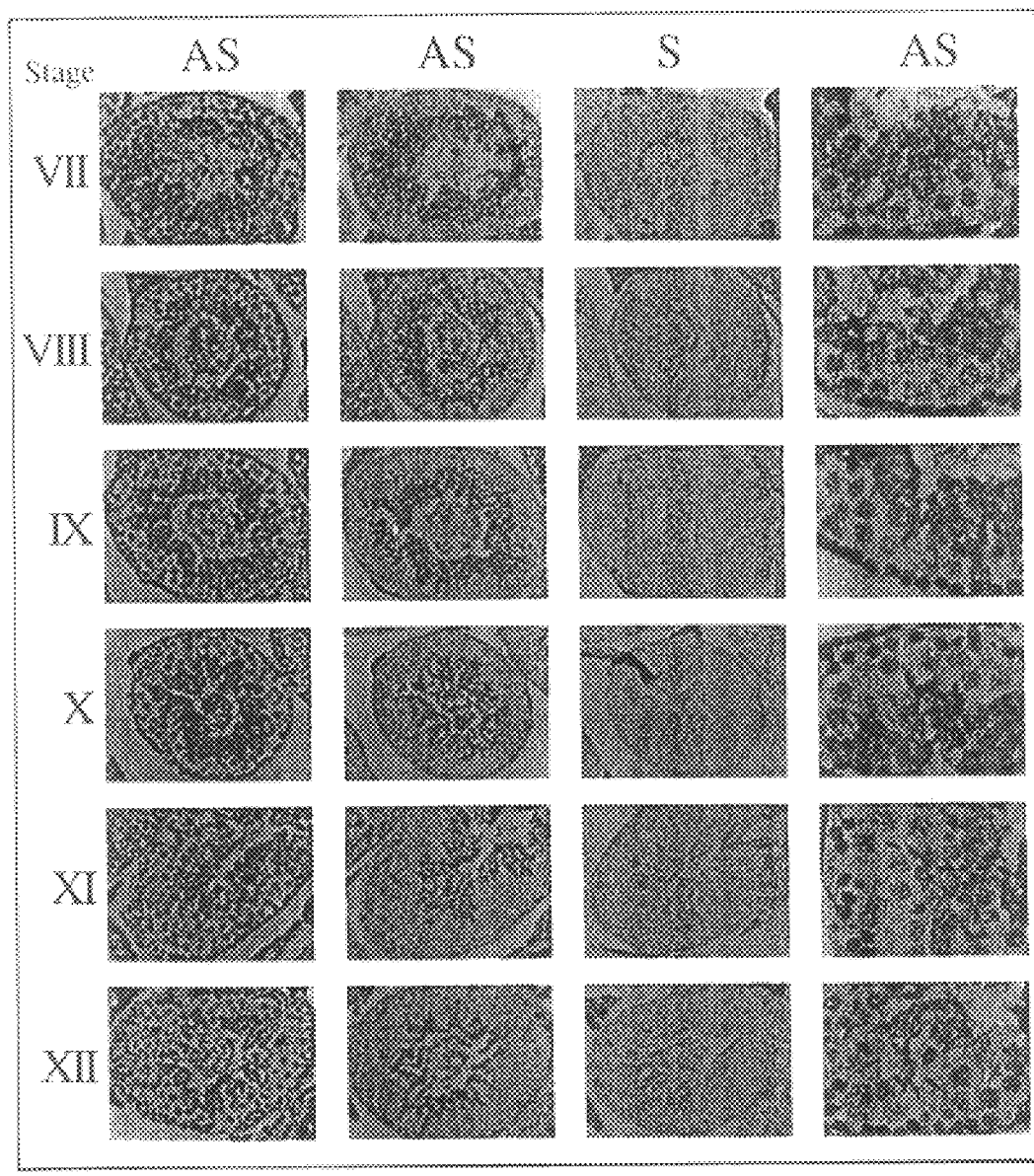
FIG. 9 shows photographs indicating the localization of the mgclh gene in various spermatogenic stages of the testis.

FIG. 8 shows photographs of seminiferous tubules of testes analyzed by in situ hybridization, each of which indicates the localization of the mgclh gene at maturation stages I to VI. FIG. 9 shows photographs of seminiferous tubules of testes analyzed by in situ hybridization, each of which indicates the localization of the mgclh gene at spermatogenic stages VII to XII.

In FIGS. 8 and 9, the first column of the photographs shows signals detected by double staining with the NBT/BCIP reagent and the safranine O, the second column of the photographs shows signals detected by single staining with the NBT/BCIP reagent, the third column of the photographs shows signals analyzed as a negative control by using the sense DIG-UTP labeled RNA probe for the in situ hybridization, and the fourth column of the photographs shows respective enlarged photographs of the photographs in the first column. As is clear from FIGS. 8 and 9, brown signals indicating the expression of the mgclh gene had been observed in round spermatids from stage I to stage XII. Interestingly, it was revealed that round spermatids exhibiting strong signals and round spermatids not exhibiting any signals were mixed in stage I, and that the distribution of the signals was spread to adjacent round spermatids and the intensity of the signals was gradually reduced, as the stage progressed. In stage V, moderate signals were observed in approximately all round spermatids. As the stage progressed, signals were gradually moved to a lumen region of the seminiferous tubule.

This phenomenon was supposed to be caused by the mgclh gene being located on the X-chromosome. That is, immediately after completing meiosis, the ratio of haploid round spermatids having X-chromosomes to haploid round spermatids having Y-chromosomes was one. Therefore, signals detecting mRNA transcribed from the mgclh gene locating on the X-chromosome was observed on only subduple haploid round spermatids in stage I. However, intercellular bridges usually exist between round spernatids, through which transfer of substances such as transcript is carried out. Therefore, the distribution of the signals detected on only round spermatids having the X-chromosome in stage I was supposed to spread to all the round spermatids over time.

Determining the significance of the intercellular bridges formed in the testis is an important biological problem. Although various theories have been proposed, evidence has been scant. As described above, the inventors have discovered and have cloned the mgclh gene locating on the X-chromosome and specifically expressed in haploid cells of the testis. The inventors have estimated that the appearance of this gene, that is, the gene specifically expressed in the haploid germ cells, is a biological factor leading to the acquisition of the intercellular bridge during evolution. That is, when the gclh gene sharing a high homology with the drosophila gcl gene is hypothesize to be an essential gene for forming germ cells (sperm) as is the drosophila gcl gene which is an essential gene for forming drosophila gern cells, the intercellular bridges are believed to be forced to form between the round spernatids due to the biological necessity. That is because only X-bearing sperm can be formed and Y-bearing sperm cannot be formed, when the intercellular bridges are not formed. Thus, the inventors have hypothesized that the gene partition of haploid round spermatids based on sex differentiation, that is, sex chromosome differentiation, is a biological factor promoting the formation of the intercellular bridge.

The novel testis-specific gene according to the present invention can be applied to the following uses.

(1) Gene Diagnosis

The entire portion or a portion of the base sequence of the gene, cDNA, or RNA, according to this invention can be used for gene diagnosis or genetic polymorphism analysis of a disease (such as infertility) based on mutations such as a single base mutation, deletion, insertion, and/or substitution. For example, the gene diagnosis or the genetic polymorphism analysis may be conducted according to the following procedures. First, genomic DNA or RNA is extracted from mammalian cells such as human cells, or livestock cells, and is purified according to a standard method Purified genomic DNA or RNA is used as a template for subsequent PCR or RT-PCR. Then, DNA in a specified region of a gene to be analyzed is amplified by means of the PCR or RT-PCR using the aforementioned template and a pair of primers constructed based on a base sequence of the gene (synthetic DNA oligomers, or a pair of a sense chain and an antisense chain).

Then, the amplified DNA fragments are subjected to Agarose Gel Electrophoresis (AGE), Degenerating Gradient Gel Electrophoresis (DGGE), Single Stranded Conformational Polymorphism (SSCP), Restriction Fragment Length Polymorphism (RFLP), Sequence Specific Thermnal Elution Chromatography (SSTEC), sequencing, or the like.

(2) Discrimination of Sex

Since the gene according to this invention is located on the X-chromosome, the gene can be used for discriminating the sex of livestock or the like. For example, the discrimination of sex may be conducted according to the following procedures. A portion of sperm fractionated by means of a cell fractionator such as a fluorescence activated cell sorter (FACS) are applied onto a slide glass, are fixed, and are then treated with a protease. Then, the aforementioned FISH analysis is conducted using a probe containing the entire portion or a portion of the gene. As the result, the sex of the fractionated sperm can be discriminated. Alternatively, DNA is extracted from cells removed from early embryos of a livestock animal immediately after fertilization. Then, the aforementioned quantitative Southern blot analysis is conducted using a portion of the gene as a probe, or alternatively, a quantitative PCR analysis such as a TaqMan method is conducted according to a conventional method. As a result, the sex of the livestock animal can be determined before delivery.

(3) Separation of Sperm

Since the gene according to this invention is located on the X-chromosome, the gene can be used for separating sperm by specifically labeling the gene and subsequently specifically separating sperm having the labeled gene from unlabeled spermn.

(4) Infertility Treatment by Introducing the Gene or the Gene Product

The gene according to this invention can be used for treatment of a disease caused by gene deletion, such as infertility, by means of introducing the entire portion or a portion of the gene or the gene product such as RNA transcribed from the gene or protein encoded by the gene according to this invention.

(5) Creation of Novel Livestock and Chromosomal Manipulation by Means of Gene Manipulation Since the gene according to this invention is located on the X-chromosome, the gene can be used for creating novel monogenic livestock by means of gene manipulation of the gene.

What is claimed is:

1. An isolated nucleotide sequence of a gene, wherein said sequence (i) is located on the X-chromosome of a mammal, (ii) is specifically expressed in haploid cells of the testis, and (iii) encodes a polypeptide having a homology of at least 95% with the amino acid sequence set forth in SEQ ID NO.2.

2. The nucleotide sequence according to claim 1, wherein the mammal is selected from the group consisting of mouse, human, and cattle.

3. The nucleotide sequence according to claim 1, wherein said sequence is set forth in SEQ ID NO: 1.

4. An isolated polynucleotide comprising a nucleotide sequence selected from the group consisting of SEQ ID NO: 1, a complement of SEQ ID NO: 1, and a fragment thereof.

5. An isolated nucleotide sequence encoding a polypeptide set forth in SEQ ID NO: 2.

* * * * *